(12) United States Patent
Fechner et al.

(10) Patent No.: US 7,192,602 B2
(45) Date of Patent: *Mar. 20, 2007

(54) WATER-INSOLUBLE, ANTIMICROBIAL SILICATE GLASS AND USE THEREOF

(75) Inventors: Jörg Hinrich Fechner, Mainz (DE); José Zimmer, Ingelheim (DE)

(73) Assignee: Schott AG, Mainz (DE)

( * ) Notice: Subject to any disclaimer, the term of this patent is extended or adjusted under 35 U.S.C. 154(b) by 129 days.

This patent is subject to a terminal disclaimer.

(21) Appl. No.: 10/487,113

(22) PCT Filed: Aug. 17, 2002

(86) PCT No.: PCT/EP02/09219

§ 371 (c)(1),
(2), (4) Date: Mar. 19, 2004

(87) PCT Pub. No.: WO03/018495

PCT Pub. Date: Mar. 6, 2003

(65) Prior Publication Data
US 2005/0069592 A1 Mar. 31, 2005

(30) Foreign Application Priority Data
Aug. 22, 2001 (DE) .................. 101 41 117

(51) Int. Cl.
*A01N 25/00* (2006.01)
*A01N 59/26* (2006.01)
*A61K 33/42* (2006.01)
*C03C 3/097* (2006.01)

(52) U.S. Cl. .................. 424/405; 424/604; 501/63
(58) Field of Classification Search .............. 424/405, 424/604; 501/63
See application file for complete search history.

(56) References Cited

U.S. PATENT DOCUMENTS

| | | | |
|---|---|---|---|
| 3,926,246 A | 12/1975 | Corbett et al. | 164/56 |
| 4,092,139 A | 5/1978 | Ference | 65/30 R |
| 4,366,253 A * | 12/1982 | Yagi | 501/63 |
| 5,034,353 A | 7/1991 | Shibuya et al. | 501/3 |
| 5,074,916 A | 12/1991 | Hench et al. | 106/35 |
| 5,290,544 A | 3/1994 | Shimono et al. | 424/63 |
| 5,639,702 A | 6/1997 | Imashita et al. | 501/44 |
| 5,733,531 A * | 3/1998 | Mitchnick et al. | 424/59 |
| 5,807,641 A | 9/1998 | Oku et al. | 428/701 |
| 5,834,008 A | 11/1998 | Greenspan et al. | 424/443 |
| 6,074,984 A * | 6/2000 | Demmel et al. | 502/439 |
| 6,123,743 A * | 9/2000 | Carman et al. | 51/307 |
| 6,143,318 A | 11/2000 | Gilchrist et al. | 424/446 |
| 6,245,732 B1 | 6/2001 | Gallon et al. | 510/507 |
| 6,589,928 B1 | 7/2003 | Lee | |
| 2002/0086039 A1 * | 7/2002 | Lee et al. | 424/401 |
| 2004/0137075 A1 * | 7/2004 | Fechner et al. | 424/601 |
| 2004/0166172 A1 * | 8/2004 | Rosati et al. | 424/601 |
| 2005/0064193 A1 * | 3/2005 | Fechner et al. | 428/406 |
| 2005/0119105 A1 * | 6/2005 | Zimmer et al. | 501/32 |

FOREIGN PATENT DOCUMENTS

| | | |
|---|---|---|
| CA | 2374395 | 1/2001 |
| CN | 1323527 | 11/2001 |
| DE | 2 239 307 | 2/1974 |
| DE | 2 346 778 | 3/1974 |
| DE | 28 00 145 | 9/1978 |
| DE | 39 39 831 | 6/1990 |
| DE | 195 03 167 | 8/1996 |
| EP | 0 425 927 | 10/1990 |
| EP | 0 921 105 | 6/1999 |
| GB | 1 294 337 | 10/1972 |
| JP | 3-146436 | 6/1991 |
| JP | 7-25635 | 1/1995 |
| JP | 7-291654 | 11/1995 |
| JP | 8-245240 | 9/1996 |
| JP | 10-218637 | 8/1998 |
| JP | 10-231187 | 9/1998 |
| JP | 11-209143 | 3/1999 |
| JP | 11-228173 | 8/1999 |
| JP | 2000-203876 | 7/2000 |
| JP | 2000-264674 | 9/2000 |
| WO | WO 97/27148 | 7/1997 |
| WO | WO 96/21628 | 7/1998 |
| WO | WO 00/15167 | 3/2000 |
| WO | WO 00/38552 | 7/2000 |
| WO | WO 00/66086 | 11/2000 |
| WO | WO 00/76486 | 12/2000 |

OTHER PUBLICATIONS

Lusvardi G, Leonelli C, Menabue L, Mortorsi M, Saladini M, "Reactivity of Vitreous Biocompatible System Na2O-CaO-P205-Ag2O-SiO2," Cimtech 98—Symposium XI, Materials in Clinical Application, Firenze, p. 271 (1998).*

Duffus JH, "Heavy Metals'- A Meaningless Term? (IUPAC Technical Report)," Pure and Applied Chemistry, vol. 74, No. 5, pp. 793-807 (2002).*

* cited by examiner

*Primary Examiner*—Johann Richter
*Assistant Examiner*—David P. Stitzel
(74) *Attorney, Agent, or Firm*—Baker & Daniels LLP

(57) ABSTRACT

The invention relates to an antimicrobial silicate glass with the following weight composition in wt. % based on oxides: $SiO_2$ 20 to 70, $Na_2O$ 5 to 30, $K_2O$ 0 to 5, $P_2O_5$ 1 to 15, $B_2O_3$ 0 to 10, CaO 4 to 30, AgO 0 to 2, ZnO 0 to 8, CuO 0 to 5, MgO 0 to 8, $Al_2O_3$ 0 to 7, $CeO_2$ 0 to 5, $Fe_2O_3$ 0 to 2 whereby the sum of the components AgO, CuO, $CeO_2$ is >10 ppm, preferably ≧100 ppm and <8 wt. %.

21 Claims, No Drawings

WATER-INSOLUBLE, ANTIMICROBIAL SILICATE GLASS AND USE THEREOF

This application claims priority, under 35 U.S.C. § 371, to PCT Patent Application No. PCT/EP02/09219, filed Aug. 17, 2002, which claims priority to German Patent Application No. 101 41 117.0, filed Aug. 22, 2001.

In this application, the term water-insoluble is understood to mean that a base glass of a glass composition does not dissolve in water, but rather only the surface reacting with the surrounding water exchanges ions. Water-soluble, antimicrobial silicate glass is known from a number of documents.

U.S. Pat. No. 5,290,544 describes water-soluble glass for use in cosmetic products with very low $SiO_2$ and very high $B_2O_3$ or high $P_2O_5$ contents. The glass has silver concentrations higher than 0.5 wt. %. This glass has an extremely low hydrolytic resistance and is prone to completely dissolve in water. The hereby released Ag and/or Cu ions have an antibacterial effect. JP-A-92178433 also describes a water-soluble glass powder with $SiO_2$<37 wt. % as a polymer additive with high silver concentrations >1 wt. %.

U.S. Pat. No. 6,143,318 describes argentiferous phosphate glass that are used as antimicrobial material for the treatment of infection wounds with combinations of Cu, Ag, and Zn. This also includes water-soluble glass that has a low $SiO_2$ concentration and a very high $P_2O_5$ content.

Another water-soluble glass that dissolves completely in water is, for example, a glass of the type described in JP-A-08245240. The glass in accordance with JP-A-08245240 has a high phosphor content.

Due to their low hydrolytic stability, these types of glass are very limited in their suitability for refining in aqueous media.

Silicate glass without an antibacterial effect is described, for example, in DE 2346778 C2. DE 2346778 C2 shows a base glass without AgO and CuO as enamel glass. DE 2239307 describes an ion-exchange glass that contains no AgO, ZnO, CuO, and $CeO_2$. Furthermore, GB 1294337 shows ion-exchangeable glass ceramics that also contains no AgO, ZnO, CuO, and $CeO_2$.

Antimicrobial argentiferous borosilicate glass or borophosphate glass is described in documents JP 10218637, JP 08245240, JP 07291654, JP 03146436, JP 2000264674, and JP 2000203876. These types of glass have, for the most part, good hydrolytic stability and can therefore be refined in aqueous media.

Zeolites, which contain silver that is introduced via ion exchange, are also used as an antibacterial substance. This is described, for example, in U.S. Pat. No. 6,245,732 and WO 0038552.

Heavy-metal-free glass, in which an antimicrobial effect can be proven, is described in DE 19932238 and DE 19932239.

Glass powders with a bioactive effective are known from WO 97/27148. However, the type of glass known from WO 97/27148 is not allowed to contain any heavy metals.

The disadvantage of the glass described in the state of the art is that many of the substances have undesirable side effects and are not harmless to health. They can be allergenic, irritating to the skin, or otherwise harmful to the human body or the environment.

Another disadvantage is that the glass known from the state of the art can only be produced commercially.

Furthermore, the glass known from the state of the art releases the ions very quickly. A controlled ion release is described in none of the documents known from the state of the art.

The problem of the invention is to specify glass or glass ceramics or glass powder that avoids the disadvantages of the state of the art. In particular, glass in terms of this application should be water-insoluble and have an antimicrobial effect.

This problem is solved by a glass or glass ceramics in accordance with one of claims 1, 3, 5, 8, or 9.

The silicate glass in accordance with the invention can be produced commercially with standard processes.

The glass or glass ceramics in accordance with the invention can be added to products in powder form. Thus, the glass is suitable for milling in different types of milling media, e.g. water; this means that the glass has a sufficient water-insolubility.

The silicate glass or the silicate glass ceramics in accordance with the invention has a biocide or a biostatic effect vis-á-vis bacteria, fungi, and viruses. It is safe on the skin when in contact with humans, is toxicologically harmless, and is especially suitable for consumption.

Based on the requirements of toxicological innocuousness of the silicate glass as well as its suitability for consumption, the glass or the glass ceramics based on the invention is particularly pure. The impact through heavy metals is low. Thus, the maximum concentration in the area of cosmetic products is preferably for Pb<20 ppm, Cd<5 ppm, As<5 ppm, Sb<10 ppm, Hg<1 ppm, and Ni<10 ppm.

With the antimicrobial substances, the products themselves can be preserved or an antimicrobial effect can be attained on the outside. Areas of application are, for example, cosmetic products, deodorant products, foods, paints, lacquers, plasters, paper-hygiene products, medical products, and cleaners.

Skin irritations play an important role in the cosmetic field. Thus, it is advantageous if the antimicrobial addition of glass is particularly gentle on the skin.

A particular advantage of the glass or glass ceramics in accordance with the invention is that the glass or the glass ceramics is suitable, based on the melting or hot shaping behavior, for being produced in appropriate commercial factories.

Besides production via a melting process, there are also alternative production processes via the sol-gel or reaction-sinter routes.

Surprisingly, there is an extremely strong antimicrobial effect of the glass in the glass composition based on the invention due to a synergistic effect between the antimicrobial effect of the Ag, Cu, Zn, and Ce heavy metal ions and the effect of the ion exchange of the glass. Through reactions on the surface of the glass, alkalis of the glass are exchanged for H+ ions of the aqueous medium. The antimicrobial effect of the ion exchange is, among other things, based on an increase in the pH value and the osmotic effect on microorganisms.

Ion-exchangeable glass in accordance with the invention has an antimicrobial effect in aqueous media through pH-value increase through ion exchange between Na or Ca and the H+ ions of the aqueous solution as well as through ion-conditional damage to cell growth (osmotic pressure, disruption of metabolic processes in the cells). Depending on the particle size, concentration, and the composition of the powder, pH values of up to 13 are reached.

The glass contains $SiO_2$ as a network former, preferably between 35 to 70 wt. %. At low concentrations, the hydrolytic stability decreases greatly so that milling in aqueous media is no longer ensured without significant dissolving of the glass. The crystallization stability can decrease at higher values and the processing temperature is clearly increased so that the melting and hot shaping properties deteriorate.

$Na_2O$ is used as the melter for the melting of the glass. At concentrations smaller than 5%, the melting behavior is negatively influenced. Moreover, the necessary mechanism of the ion exchange is no longer sufficient enough to attain an antibacterial effect. At $Na_2O$ concentrations higher than 30%, a deterioration of the chemical resistance or hydrolytic stability, in particular in connection with a decrease in the $SiO_2$ content, is observed.

$P_2O_5$ is a network former and can increase the crystallization stability. The concentrations should not be above 15 wt. %, since otherwise the chemical stability of the silicate glass decreases too much. $P_2O_5$ improves the surface reactivity of the glass.

CaO improves the chemical stability, in particular in the slightly alkaline range and is thus necessary in order to prevent the glass from dissolving in aqueous media.

Additions of $K_2O$ promote the exchangeability of the sodium, or rather the potassium can be exchanged for H+ ions.

The amount of $Al_2O_3$ can be increased up to a maximum of 8 wt. % in order to increase the chemical stability of the crystallization stability. ZnO is an important component for the hot shaping properties of the glass. It improves the crystallization stability and increases the surface tension. Moreover, it can support the antimicrobial effect. It increases the crystallization stability at low contents of $SiO_2$. Up 8 wt. % ZnO can be contained in order to obtain an antimicrobial effect. A preferred embodiment contains <4 wt. % ZnO or <2 wt. %. Embodiments with <1 wt. % or 0.5 wt. % or rather <0.1 wt. % are especially preferred.

AgO, CuO, $CeO_2$ are antimicrobial additives that synergistically strengthen the intrinsic antimicrobial effect of the base glass so that relatively low concentrations need to be added.

In order to obtain the desired antimicrobial effect, the glass preferably contains <2 wt. % or 1 wt. % AgO, CuO, $CeO_2$. A preferred embodiment contains <0.5 wt. % or 0.2 wt. % AgO, CuO, $CeO_2$. A particularly preferred embodiment contains contents of <0.1 or 0.01 AgO, CuO, $CeO_2$ whereby the lower active amount is 0.001 wt. % AgO, CuO, $CeO_2$.

The sum of the contents of AgO, ZnO, CuO, and $CeO_2$ lies <8 wt. % or 5 wt. %. In a preferred embodiment, the amount is <2 wt. % or 1 wt. %. A preferred embodiment contains amounts of <0.5 or 2 wt. %. A particularly preferred embodiment has contents of <0.1, 0.05, or 0.01 wt. %, whereby 0.001 wt. % is preferably used as the lower effective amount.

The sum of the contents of AgO, CuO, ZnO and $CeO_2$ in glass that contains more than one of these components lies below the added amounts in glass that only contains one of these oxide components due to synergistic effects.

The glass based on the invention has no skin-irritating effects. In fact, some anti-inflammatory effects are even observed.

Through a combination of the pH effect and the Ag release, a considerable increase can be achieved in the antimicrobial effect that goes beyond the sum of the individual effects. The concentration of Ag ions released in the product can thus lie clearly below 1 ppm.

The introduction of the Ag can hereby take place either already during the melting through corresponding silver salts or through ion exchange of the glass after the melting.

In order to obtains coloring effects, individual or several coloring components like e.g. $Fe_2O_3$, CoO, CuO, $V_2O_5$, $Cr_2O_5$ can be added to the glass in a total concentration smaller than 4 wt. %, preferably smaller than 1 wt. %.

Glass within the required composition range meets all requirements with respect to use in the areas of paper hygiene, cosmetics, paints, lacquers, plasters, medical products, cosmetic uses, food additives as well as use in deodorant products.

The glass can be used as glass powder, whereby particle sizes <100 μm are obtained through a milling process. Particle sizes <50 μm or <20 μm have proven to be appropriate. Particle sizes <10 μm as well as smaller than 5 μm are particularly suitable. Particle sizes <1 μm have proven to be particularly suitable. The milling process can be performed dry as well as with aqueous and non-aqueous milling media.

An important property, also of the glass powder, is the surprisingly proven safeness on skin, which is also present at high concentrations with high pH values.

The glass can be used in each suitable form including the named powder form. Mixtures of different glass powders from the composition range with different compositions are also possible. The mixture with other glass powders is also possible in order to combine certain effects.

Depending on the area of application, components like fluorine can be added to the glass at total concentrations of up to 5 wt. %.

The total metal ion release of the glass in order to achieve sufficient biocide or preservative effects in a product can be <50 ppm, 10 ppm based on the synergistic effect. A preferred embodiment gives <1 ppm, in particular <100 ppb, for pH values between 9 and 13 pH.

The glass described in this invention is not water-soluble, but rather works mainly through ion exchange or ion release, which is associated with a surface reaction, pH increase, and metal ion release. Through the synergistic, antimicrobial effect of the glass itself as well as the antimicrobial effect of the metal ions, the required amounts of metal ions are lower, in order to achieve an appropriate effect.

The invention is described below using the embodiment examples.

Embodiments

The glass was melted from the raw materials in a platinum crucible at 1600° C. and was processed into a semi-finished product or ribbons. The ribbons were milled in a drum grinder to grain sizes of up to 4 μm. Grain sizes below 4 μm were attained with attritor grindings in an aqueous or non-aqueous medium.

TABLE 1

Compositions of glass in accordance with the invention.

| | 1 | 2 | 3 | 4 | 5 | 6 | 7 |
|---|---|---|---|---|---|---|---|
| $SiO_2$ | 42.8 | 42.9 | 43 | 43 | 36 | 53.6 | 58.4 |
| $P_2O_5$ | 7 | 7 | 7 | 7 | 6 | 6 | 6 |
| CaO | 25 | 25 | 25 | 25 | 29.5 | 20.2 | 17.8 |
| $Na_2O$ | 25 | 25 | 25 | 25 | 29.5 | 20.2 | 17.8 |
| AgO | 0 | 0.1 | 0.01 | 0.001 | 0.01 | 0.1 | 0.01 |
| ZnO | 0 | 0 | 0 | 0 | 0 | 0 | 0 |
| CuO | 0 | 0 | 0 | 0 | 0 | 0 | 0 |
| $K_2O$ | 0 | 0 | 0 | 0 | 0 | 0 | 0 |
| MgO | 0 | 0 | 0 | 0 | 0 | 0 | 0 |
| $Al_2O_3$ | 0 | 0 | 0 | 0 | 0 | 0 | 0 |

TABLE 1-continued

Compositions of glass in accordance with the invention.

| | | | | | | |
|---|---|---|---|---|---|---|
| CeO$_2$ | 0.2 | 0 | 0 | 0 | 0 | 0 | 0 |

| | 8 | 9 | 10 | 11 | 12 | 13 |
|---|---|---|---|---|---|---|
| SiO$_2$ | 58.4 | 58.4 | 45 | 45 | 43 | 35 |
| P$_2$O$_5$ | 6 | 6 | 6 | 5.5 | 6 | 6 |
| CaO | 17.8 | 17.8 | 24.5 | 23.5 | 25 | 29 |
| Na$_2$O | 17.8 | 17.8 | 23.9 | 24.5 | 25 | 29 |
| AgO | 0.1 | 0.1 | 0.1 | 0.1 | 1.0 | 1.0 |
| ZnO | 5 | 0 | 0 | 0 | 0 | 0 |
| CuO | 0 | 2 | 0 | 0 | 0 | 0 |
| K$_2$O | 0 | 0 | 0.5 | 0 | 0 | 0 |
| MgO | 0 | 0 | 0 | 1 | 0 | 0 |
| Al$_2$O$_3$ | 0 | 0 | 0 | 0.5 | 0 | 0 |
| CeO$_2$ | 0 | 0 | 0 | 0 | 0 | 0 |

Particularly preferred are thus compositions of glass in accordance with the invention that comprise 32 to 48 wt. % SiO$_2$; 5 to 7 wt. % P$_2$O$_5$; 23 to 32 wt. % CaO; 23 to 32 wt. % Na$_2$O; 0.01 to 2 wt. % Ag. These types of glass compositions have the advantage of a clearly higher reactivity. Furthermore, they have a high water-insolubility. Through the phosphor integrated into the SiO$_2$ network, the network is modified so that Ag is released very slightly. Ca serves as a stabilizer and reduces the solubility of the glass. In the preferred embodiment examples, the ratio of Ca to phosphor content is selected so that a controlled and slow ion release is reached with a high resistance. The particularly preferred Ca/P ratio is 17/6, preferred 25/6, particularly preferred 30/6. If the ratio of Ca/P content thus lies in the 2.0–6.0 range, preferably in the 2.5 to 5.5 range, then a controlled and slow ion release is reached at a high glass resistance.

Embodiment 2 displays the following antimicrobial effect of a 0.01 wt. % aqueous suspension of a powder from a glass in accordance with European Pharmacopoeia (3rd Edition) as per Table 2.

TABLE 2

| | E. coli | P. aeruginosa | S. aureus | C. albicans | A. niger |
|---|---|---|---|---|---|
| 2 Days | 0 | 0 | 0 | 0 | 36000 |
| 7 Days | 0 | 0 | 0 | 0 | 100 |
| 14 Days | 0 | 0 | 0 | 0 | 0 |
| 21 Days | 0 | 0 | 0 | 0 | 0 |
| 28 Days | 0 | 0 | 0 | 0 | 0 |

The powder itself, including a glass in accordance with embodiment 2 in non-suspended form, has the following antimicrobial effect in accordance with European Pharmacopoeia (3rd Edition) as per Table 3.

TABLE 3

| | E. coli | P. aeruginosa | S. aureus | C. albicans | A. niger |
|---|---|---|---|---|---|
| 2 Days | 0 | 0 | 0 | 0 | 0 |
| 7 Days | 0 | 0 | 0 | 0 | 0 |
| 14 Days | 0 | 0 | 0 | 0 | 0 |
| 21 Days | 0 | 0 | 0 | 0 | 0 |
| 28 Days | 0 | 0 | 0 | 0 | 0 |

Table 4 shows a silver concentration in an aqueous suspension for a powder, including a glass in accordance with embodiment 2, after different periods of time.

TABLE 4

| | 0.1% Suspension | 1% Suspension | 10% Suspension |
|---|---|---|---|
| Ag Content after 2 h | 0.0127 mg/l | <1 ppm | <1 ppm |
| Ag Content after 24 h | <1 ppm | <1 ppm | <1 ppm |

In comparison, Table 5 shows the silver concentration in an aqueous suspension of a powder, including a glass in accordance embodiment 3, after different periods of time.

TABLE 5

| | 0.1% Suspension | 1% Suspension | 10% Suspension |
|---|---|---|---|
| Ag Content after 2 h | <1 ppm | <1 ppm | <1 ppm |
| Ag Content after 24 h | <1 ppm | <1 ppm | <1 ppm |

As follows from Tables 1 through 5, the glass based on the invention has an antimicrobial and preservative as well as a strong antimicrobial effect even at low heavy-metal release and a low toxicity.

Thus, the glass is excellent as an antimicrobial additive for a variety of uses.

The invention claimed is:

1. Water-insoluble, antimicrobial silicate glass powder, whereby the glass composition comprises the following components in wt. % based on oxides:
SiO$_2$ 32 to 48
Na$_2$O 23 to 32
P$_2$O$_5$ 5 to 7
CaO 23 to 32
AgO 0.01 to 2
whereby the ratio of Ca/P lies in the range 2.0 to 6.0, and the size of the particles of the glass powder is <100 μm; and
wherein the maximum concentrations of heavy metals are:
Pb<20 ppm, Cd<5 ppm, As<5 ppm, Sb<10 ppm, Hg<1 ppm, and Ni<10 ppm.

2. Water-insoluble, antimicrobial silicate glass powder in accordance with claim 1, characterized in that the composition in wt. % based on oxides further comprises:
K$_2$O 0 To 5
ZnO 0 to 8
CuO 0 to 5
MgO 0 to 5
Al$_2$O$_3$ 0 to 7
CeO$_2$ 0 to 5
Fe$_2$O$_3$ 0 to 2
whereby the sum of the components AgO, CuO, CeO$_2$ is >10 ppm and <8 wt. %.

3. Water-insoluble, antimicrobial silicate glass powder in accordance with claim 1, characterized in that the antimicrobial silicate glass contains ZnO in the range of 5 to 8 wt. % based on oxides.

4. Water-insoluble antimicrobial silicate glass powder including an antimicrobial silicate glass in accordance with claim 1, characterized in that the size of the particles of the glass powder is <5 μm.

5. Water-insoluble, antimicrobial silicate glass powder in accordance with claim 4, characterized in that particles with a size <5 μm can be obtained through attritor grinding of the glass in water.

6. Process for the production of an antimicrobial glass powder in accordance with claim 1 comprising the following steps:
   a glass is melted from raw materials;
   the melted glass is processed into ribbons;
   the ribbons are ground into glass powder, whereby the size of the particles <100 μm.

7. Water-insoluble, antimicrobial silicate glass powder in accordance with claim 1, wherein the size of the particles of the glass powder is <50 μm.

8. Water-insoluble, antimicrobial silicate glass powder in accordance with claim 1, wherein the size of the particles of the glass powder is <20 μm.

9. Water-insoluble, antimicrobial silicate glass powder in accordance with claim 1, wherein the size of the particles of the glass powder is <2 μm.

10. Water-insoluble, antimicrobial silicate glass powder in accordance with claim 1, wherein the sum of the components AgO, CuO, $CeO_2$ is >100 ppm.

11. The process of claim 6, wherein the size of the particles is <50 μm.

12. The process of claim 6, wherein the size of the particles is <20 μm.

13. A cosmetic product including the water-insoluble, antimicrobial silicate glass powder of claim 1.

14. A deodorant product including the water-insoluble, antimicrobial silicate glass powder of claim 1.

15. A food product including the water-insoluble, antimicrobial silicate glass powder of claim 1.

16. A paint including the water-insoluble, antimicrobial silicate glass powder of claim 1.

17. A plaster including the water-insoluble, antimicrobial silicate glass powder of claim 1.

18. A paper-hygiene product including the water-insoluble, antimicrobial silicate glass powder of claim 1.

19. A medical product including the water-insoluble, antimicrobial silicate glass powder of claim 1.

20. A cleaner including the water-insoluble, antimicrobial silicate glass powder of claim 1.

21. A lacquer including the water-insoluble, antimicrobial silicate glass powder of claim 1.

* * * * *